US00PP22264P2

(12) United States Plant Patent
Bernuetz

(10) Patent No.: US PP22,264 P2
(45) Date of Patent: Nov. 22, 2011

(54) ***CHRYSOCEPHALUM* PLANT NAMED 'BONCHRYKI'**

(50) Latin Name: *Chrysocephalum apiculatum*
Varietal Denomination: Bonchryki

(75) Inventor: Andrew Bernuetz, Silverdale (AU)

(73) Assignee: Bonza Botanicals Pty. Ltd., Yellow Rock, New South Wales (AU)

( * ) Notice: Subject to any disclaimer, the term of this patent is extended or adjusted under 35 U.S.C. 154(b) by 111 days.

(21) Appl. No.: 12/658,046

(22) Filed: Feb. 1, 2010

(51) Int. Cl.
*A01H 5/00* (2006.01)

(52) U.S. Cl. ..... Plt./263.1

(58) Field of Classification Search ..... Plt./263.1
See application file for complete search history.

(56) References Cited

U.S. PATENT DOCUMENTS

PP19,175 P2 * 9/2008 Bunker ..... Plt./263.1
PP19,396 P2 * 10/2008 Bunker ..... Plt./263.1
PP19,546 P2 * 12/2008 Smith ..... Plt./263.1

OTHER PUBLICATIONS

UPOV ROM GTITM Computer Database, GTI Jouve Retrieval Software 2011/01 Citation for 'Bonchryki'.*

* cited by examiner

*Primary Examiner* — Wendy C Haas
(74) *Attorney, Agent, or Firm* — C. A. Whealy

(57) ABSTRACT

A new and distinct cultivar of *Chrysocephalum* plant named 'Bonchryki', characterized by its compact, low spreading and mounding plant habit; pubescent greyed green-colored leaves, stems and peduncles; freely flowering habit; bright yellow-colored inflorescences that are positioned above and beyond the foliar plane; and good garden performance.

1 Drawing Sheet

Botanical designation: *Chrysocephalum apiculatum.*
Cultivar denomination: 'BONCHRYKI'.

BACKGROUND OF THE INVENTION

The present invention relates to a new and distinct cultivar of *Chrysocephalum* plant, botanically known as *Chrysocephalum apiculatum* and hereinafter referred to by the name 'Bonchryki'.

The new *Chrysocephalum* plant is a product of a planned breeding program conducted by the Inventor in Yellow Rock, New South Wales, Australia. The objective of the breeding program is to develop new mounding and spreading *Chrysocephalum* plants with freely and continuous flowering habit.

The new *Chrysocephalum* plant originated from an open-pollination in Yellow Rock, New South Wales, Australia, of a proprietary selection of *Chrysocephalum apiculatum* identified as code number 00-58, not patented, as the female, or seed, parent with an unknown proprietary selection of *Chrysocephalum apiculatum* as the male, or pollen, parent. The new *Chrysocephalum* plant was discovered and selected by the Inventor as a single flowering plant from within the progeny of the stated open-pollination in a controlled environment in Yellow Rock, New South Wales, Australia in March, 2007.

Asexual reproduction of the new *Chrysocephalum* plant by vegetative cuttings in a controlled environment in Yellow Rock, New South Wales, Australia since April, 2007 has shown that the unique features of this new *Chrysocephalum* plant are stable and reproduced true to type in successive generations.

SUMMARY OF THE INVENTION

Plants of the new *Chrysocephalum* have not been observed under all possible environmental and cultural conditions. The phenotype may vary somewhat with variations in environment and cultural practices such as temperature and light intensity without, however, any variance in genotype.

The following traits have been repeatedly observed and are determined to be the unique characteristics of 'Bonchryki'. These characteristics in combination distinguish 'Bonchryki' as a new and distinct cultivar of *Chrysocephalum:*

1. Compact, low spreading and mounding plant habit.
2. Pubescent greyed green-colored leaves, stems and peduncles.
3 Freely flowering habit.
4. Bright yellow-colored inflorescences that are positioned above and beyond the foliar plane.
5. Good garden performance.

Plants of the new *Chrysocephalum* differ from plants of the female parent selection in the following characteristics:

1. Plants of the new *Chrysocephalum* have greyed green-colored leaves whereas plants of the female parent selection have green-colored leaves.
2. Plants of the new *Chrysocephalum* have bright yellow-colored flowers whereas plants of the female parent selection have dark yellow-colored flowers.

Plants of the new *Chrysocephalum* can be compared to plants of *Chrysocephalum* 'Desert Flame', not patented. In side-by-side comparisons conducted in Yellow Rock, New South Wales, Australia, plants of the new *Chrysocephalum* differed from plants of the 'Desert Flame' in the following characteristics:

1 Plants of the new *Chrysocephalum* were more mounding than and not as upright as plants of the 'Desert Flame'.
2. Leaves of plants of the new *Chrysocephalum* were elongated whereas leaves of plants of the 'Desert Flame' were spatulate in shape.

3. Plants of the new *Chrysocephalum* were more freely flowering than plants of the 'Desert Flame'.

BRIEF DESCRIPTION OF THE PHOTOGRAPHS

The accompanying colored photographs illustrate the overall appearance of the new *Chrysocephalum* plant, showing the colors as true as it is reasonably possible to obtain in colored reproductions of this type. Colors in the photographs may differ slightly from the color values cited in the detailed botanical description which accurately describe the colors of the new *Chrysocephalum* plant.

The photograph at the top of the sheet comprises a side perspective view of a typical flowering plant of 'Bonchryki' grown in a container.

The photograph at the bottom of the sheet is a close-up view of a typical flowering plant of 'Bonchryki'.

DETAILED BOTANICAL DESCRIPTION

The aforementioned photographs and following observations, measurements and values describe plants grown in 15-cm containers in Higashiomi, Shiga, Japan, under commercial practice during the summer in an outdoor nursery with day temperatures ranging from 20° C. to 30° C. and night temperatures ranging from 15° C. to 20° C. Plants were pinched one time at planting. Plants were four months old when the photographs and the description were taken. In the following description, color references are made to The Royal Horticultural Society Colour Chart, 2001 Edition, except where general terms of ordinary dictionary significance are used.

Botanical classification: *Chrysocephalum apiculatum* 'Bonchryki'.

Parentage:

*Female, or seed, parent.*—Proprietary selection of *Chrysocephalum apiculatum* identified as code number 00-58, not patented.

*Male, or pollen, parent.*—Proprietary selection of *Chrysocephalum apiculatum,* not patented.

Propagation:

*Type.*—By vegetative cuttings.

*Time to initiate roots, summer.*—About 7 days at temperatures of 20° C. to 25° C.

*Time to initiate roots, winter.*—About 10 days at temperatures of 15° C. to 20° C.

*Time to produce a rooted young plant, summer.*—About three weeks at temperatures of 20° C. to 25° C.

*Time to produce a rooted young plant, winter.*—About four weeks at temperatures of 15° C. to 20° C.

*Root description.*—Fibrous; white in color.

*Rooting habit.*—Freely branching; moderately dense.

Plant description:

*Plant form/habit.*—Compact, low spreading and mounded plant habit; moderately vigorous growth habit; freely branching habit with about 77 lateral branches developing after pinching.

*Plant height.*—About 23 cm.

*Plant width* (*spread*).—About 46 cm.

*Lateral branches.*—Length: About 20.8 cm. Diameter: About 1.4 mm. Internode length: About 2.9 cm. Aspect: Upright to decumbent. Texture: Tomentose. Color: Close to 191B.

Foliage description:

*Arrangement.*—Alternate, simple; sessile.

*Length.*—About 3.8 cm.

*Width.*—About 0.8 cm.

*Shape.*—Elongated.

*Apex.*—Apiculate.

*Base.*—Rounded.

*Margin.*—Entire.

*Texture, upper surface.*—Moderately pubescent.

*Texture, lower surface.*—Densely pubescent.

*Venation pattern.*—Pinnate; reticulate.

*Color.*—Developing and fully expanded leaves, upper surface: Close to 189A; venation, close to 147D. Developing and fully expanded leaves, lower surface: Close to 191A; venation, close to 147D.

Inflorescence description:

*Appearance/flowering habit.*—Composite inflorescence form with disc florets surrounded by showy involucral bracts; inflorescences face upright and are positioned above and beyond the foliar plane; freely flowering habit with about 8 to 16 inflorescences developing per lateral branch.

*Fragrance.*—Faintly fragrant; pleasant.

*Flowering season.*—Plants flower from spring through autumn in Australia; flowering continuous during this period; plants begin flowering about five weeks after planting.

*Inflorescence longevity.*—Inflorescences last about two weeks on the plant; inflorescences persistent.

*Inflorescence bud.*—Height: About 3.7 mm. Diameter: About 4 mm. Shape: Ovoid. Color: Close to 9A.

*Inflorescence size.*—Diameter: About 6 mm. Depth (height): About 7 mm. Disc diameter: About 5.8 mm.

*Disc florets.*—Arrangement: Massed at center of receptacle. Shape: Tubular to filiform to tubular. Apex: Five-pointed. Length: About 4.9 mm. Width: About 0.9 mm. Texture: Smooth, glabrous. Color, immature: Close to 145D. Color, mature: Close to 23A.

*Involucral bracts.*—Number per inflorescence: About 39 arranged in several whorls. Length: About 3.7 mm. Width: About 0.6 mm. Shape: Lanceolate. Apex: Acute. Base: Rounded. Margin: Entire; ciliate. Texture, upper and lower surfaces: Smooth, glabrous. Color, upper and lower surfaces: Close to 6B.

*Peduncles.*—Length: About 5.4 mm. Diameter: About 0.7 mm. Texture: Tomentose. Color: Close to 194B.

*Reproductive organs.*—Present on disc florets only. Androecium: Anther length: Less than 1 mm. Anther shape: Lanceolate. Anther color: Close to 9A. Pollen amount: Moderate. Pollen color: Yellow. Gynoecium: Pistil length: About 4.5 mm. Stigma shape: Two-parted. Stigma color: Close to 23A. Style color: Close to 145D. Ovary color: Close to 145D.

*Seeds/fruits.*—Seed and fruit development have not been observed on plants of the new *Chrysocephalum.*

Disease/pest resistance: Plants of the new *Chrysocephalum* have not been noted to be resistant to pathogens and pests common to *Chrysocephalum* plants.

Garden performance: Plants of the new *Chrysocephalum* have been observed to have good garden performance and to tolerate rain, wind and temperatures ranging from about −3° C. to about 50° C.

It is claimed:

1. A new and distinct *Chrysocephalum* plant named 'Bonchryki' as illustrated and described.

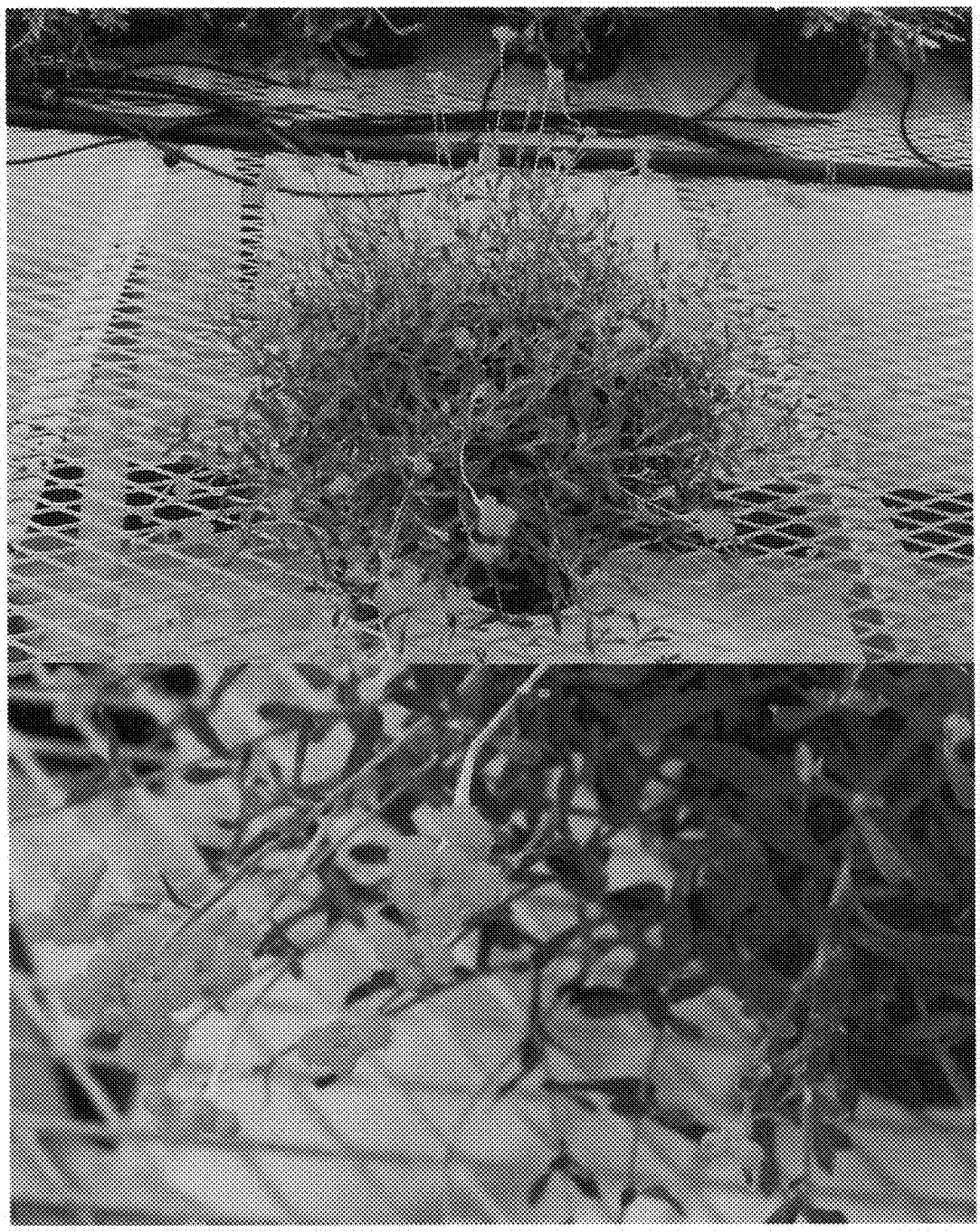

* * * * *